United States Patent [19]

Johan et al.

[11] 3,979,259

[45] Sept. 7, 1976

[54] PROCESS FOR THE PRODUCTION OF FERMENTATION BROTH WITH INCREASED VITAMIN $B_{12}$ CONTENT BY SYNCHRONIZING THE BACTERIUM POPULATION

[75] Inventors: Belá Johan; László Szemler; Tamás Szontagh; László Kuti; Emilia Simonovits; Judit Bekes née Erdös; Dénes Szekely; János Kiss; Erzsébet Kovacs née Komoroczy; Aniko Hargitai née Franyó, all of Budapest, Hungary

[73] Assignee: Richter Gedeon Vegyeszeti Gyar Rt., Budapest, Hungary

[22] Filed: Oct. 24, 1974

[21] Appl. No.: 517,788

[30] Foreign Application Priority Data
Oct. 26, 1973 Hungary................................ RI 524

[52] U.S. Cl............................................ 195/28 VB
[51] Int. Cl.$^2$.......................................... C12D 5/06
[58] Field of Search................................ 195/28 VB

[56] References Cited
FOREIGN PATENTS OR APPLICATIONS
265,043   6/1970   U.S.S.R. .......................... 195/28 VB

*Primary Examiner*—Alvin E. Tanenholtz
*Attorney, Agent, or Firm*—Karl F. Ross; Herbert Dubno

[57] ABSTRACT

The invention relates to a process for the production of a fermentation broth with increased vitamin $B_{12}$ content by a fermentation process carried out with a methane-producing mixed bacterium population under anaerobic septic conditions in the presence of known nutrient components and precursors. According to the invention, methanol, preferably in an amount of 0.5 v/v %, is added for some days, preferably for 3 days to the fermentation broth containing vitamin $B_{12}$ used as the starting substance. Thereafter a minor part, preferably 10% of the fermentation broth, is removed and an equal volume of a nutrient broth containing the usual components in tenfold concentrations is added periodically in every 5th to 12th day, then the removal of fermentation broth is interrupted for 0 to 2 days, preferably for 1 day, and only 0.4 to 1.5 v/v% of methanol are added to the fermentation broth, and subsequently a minor part, preferably 10% of the fermentation broth, is removed daily and an equal volume of a nutrient broth containing the usual components in the usual concentrations is added together with 0.4 to 1.5 v/v % of methanol, depending on the biogas production of the fermentation broth. This series of operations is repeated periodically during the complete fermentation procedure taking into consideration the pH of the fermentation broth.

2 Claims, No Drawings

PROCESS FOR THE PRODUCTION OF FERMENTATION BROTH WITH INCREASED VITAMIN $B_{12}$ CONTENT BY SYNCHRONIZING THE BACTERIUM POPULATION

This invention relates to a process for the production of fermentation broth with increased vitamin $B_{12}$ content, by anaerobic fermentation carried out with a methane-producing mixed bacterium population under septic conditions.

As is known, vitamin $B_{12}$ is generally produced either by monocultural sterile fermentation or with a mixed bacterium population of sewage sludge origin, adapted to a special culture medium (British patent specification No. 1,169,933).

It is also known that when using a mixed bacterium population, by contrast with the sterile monocultural fermentation process, the yield of vitamin $B_{12}$ cannot be increased in practice by increasing the individual productivities of the bacterium strains. This can be attributed to the fact that in mixed cultures the metabolic processes of the individual bacterium strains are not independent of each other. Their interaction may be positive, leading sometimes to a very marked increase in the production of the desired metabolite (B. Johan, A. Szabó, E. Keresztessy: Combined fermentation Acta Microbiol. Acad. Sci. Hung. VI/4 (1959), but it may also be negative, for instance in septic fermentations where the common pathogenic bacteria are unable to proliferate in the fermentation broth.

Several methods are known for increasing the vitamin $B_{12}$ yields of fermentations carried out with methane-producing mixed bacterium populations, these methods can usually be applied, however, to the production of fermentation broths containing only about 10,000 to 11,500 $\mu g./l.$ of vitamin $B_{12}$ (e.g. Hungarian patent specification No. 159.356).

The aim of the present invention is to provide an economical process for increasing the yield of vitamin $B_{12}$ in the fermentation processes utilizing known, semicontinuously maintained bacterium populations of sewage origin. The new process was developed by taking into account the following facts and experimental results:

1. Investigations of the vitamin $B_{12}$-producing sewage-originated methanobacterial fermentation have revealed that 93 to 97% of the resulting vitamin accumulates in the microorganism cells, and enters the broth (supernatant) only after the necrosis of the bacteria (B. Johan: Acta Microbiol. Acad. Sci. Hung. 17, 319–328 (1970). Thus, in order to increase the vitamin $B_{12}$ yield of the fermentation, the number of vitamin-producing bacteria should be increased.

2. The bacteria of the methane-producing bacterium population of sewage sludge origin, particularly the coccus-diplococcus bacteria, have a relatively prolonged duplication period, and thus they have no real "logarithmic phase" characteristic of the reproduction of most bacteria. Their reproduction corresponds rather to the "arithmetic linear growth" described by Lamana and Mallette (Basic Bacteriology, 368(1965). It is also known that, under appropriate conditions, these bacteria multiply by bipartition, i.e. two bacteria are formed from one. Under appropriate environmental conditions the bacteria, already in the multiplication stage, continue to duplicate, but otherwise the bacteria reach a repose period. Once the repose period has been reached, the bacteria start to multiply again after only a more or less prolonged "lag" phase upon an appropriate change in the oecological conditions. This is the reproduction cycle of bacteria. The bacteria of any given culture are in the most diverse phases of their reproduction cycles.

3. Upon measuring daily the bacterium content and vitamin $B_{12}$ content of a fermentation broth produced in a semicontinuous fermentation (10% of the fermentation broth are removed daily and a same amount of fresh nutrient broth is supplied), these values are found to be approximately invariable, that is, within 24 hours both the number of the bacteria and the amount of vitamin $B_{12}$ return to the levels observed before removal. This phenomenon can be illustrated schematically as follows: when 10% of a fermentation broth, containing initially 100 units (millions or billions) of bacteria, are removed and a fresh nutrient broth with the same volume is supplied, the fermentation broth diluted with the fresh nutrient broth will contain only 90 units of bacteria. By the next day, however, this number increases again to 100. The simplest explanation of this phenomenon is that in this instance only 10 units of the 90 units of bacteria present have undergone bipartition, i.e. 20 units have been formed from 10, which, together with the unpartitioned 80 units yield 100, the original number of bacteria.

In order to reach a higher number of bacteria and thus an increase in the vitamin $B_{12}$ yield, instead of only ten units, the possible highest number of bacteria must be forced to undergo bipartition at the same time, thereby raising the number of bacteria present in the fermentation broth above the previous level. This can be accomplished by bringing as many bacteria as possible onto the same phase of the reproduction cycle, i.e. by synchronizing their reproduction.

Thus the invention is based on achieving the most perfect synchronization of the reproduction cycle of the bacterium mass, both at the start of a new fermentation and during the semicontinuous maintenance of the fermentation broth with an already high vitamin $B_{12}$ content.

According to the invention one proceeds as follows: a semicontinuously maintained fermentation broth with a vitamin $B_{12}$ content of about 10.000 $\mu g./l.$ is used as the starting material, and only a small amount of methanol is added to the broth for three days, to bring the population by starvation into a state where the partition of the bacteria in the multiplication phase ceases and new partition cannot start owing to the lack of nutrient. Thus the cells are induced to undergo a "stationary" or lag phase. On the fourth day, a nutrient broth, which contains the usual components in tenfold concentration, is added at once to the fermentation broth. This nutrient broth is designated in the following as "concentrated broth". Upon the addition of the concentrated broth the cells in the synchronized repose period start to multiply, and the bacterium number of the fermentation broth surpasses the previous level. However, owing to the fact that the bacteria are in different stages of the repose period (in the stationary or lag stages, respectively), their bipartition starts with a certain difference in time; thus the population is, to a certain extent, desynchronized again. Since the concentrated broth necessary to the maintenence of the metabolism of the increased number of bacteria is introduced only periodically, e.g. at intervals of 5 to 12 days, close to the end of these periods the amount of nutrient will be insufficient again, involving a relative starvation, which causes the bacterium population or a part thereof to synchronize again in an inactive (repose) period. According to our observations, the insufficiency of nutrient is indicated by a decrease in pH to 5.5 – 5.8. At this point the next batch of the concentrated broth is added. This procedure is also continued in the semi-continuous phase of fermentation. In this phase 10% of the fermentation broth is removed daily, and an equal volume of a nutrient broth containing the usual components in the usual (normal) concentrations (i.e. in 10 times lower concentrations than in the concentrated broth) is added to the remainder of the fermentation broth. This latter nutrient broth is termed in the following as "usual broth or normal broth". The addition of the concentrated broth necessary to the multiplication of the increased number of bacteria is carried out periodically, in every 5th to 12th day in average. When the concentrated broth is added on the average every 10th day, 10% of the fermentation broth is removed and replaced with an equal amount of usual broth in the intercurrent days, and an appropriate amount of methanol is added, 30,000 to 40,000 $\mu g./l.$ concentrations of vitamin $B_{12}$ can be reached and steadily maintained.

If the procedure is started with a semicontinuous fermentation, and a broth with a vitamin $B_{12}$ content of 10,000 $\mu g./l.$ is used, 10 to 25 days are required to reach the 30,000 $\mu g./l.$ level of vitamin $B_{12}$. Since at this level the semicontinuous fermentation can be maintained continuously, the invested time can be recovered after rendering the procedure semicontinuous. The fact that the vitamin level can also be increased according to the process of the invention even in a simultaneous semicontinuous fermentation (see Examples 2 and 3) increases the economy of the process.

According to the process of the invention one can also raise the starting low (e.g. 10,000 $\mu g./l.$) vitamin $B_{12}$ level to the desired high (e.g. 30,000 $\mu g./l$) level, by preparing a "fermentation broth concentrate" (in fact, bacterium concentrate). Accordingly, another fermentation broth is separated, and the concentrate, containing about 80,000 to 90,000 $\mu g./l.$ of vitamin $B_{12}$, is added to the starting broth with low vitamin $B_{12}$ level in an amount required to adjust its vitamin $B_{12}$ lvel to e.g. 20,000 $\mu g./l.$ Thereafter the fermentation is carried out according to the synchronization method as described above. This method is the "enriched synchronous method", which can be performed semicontinuously already from the start, as described in Example 3.

Our experiments have shown that, of the additives utilized in the fermentation process, the amount of methanol introduced has an outstanding significance. There is a unanimous and linear correlation between the amounts of introduced methanol and the biogas formed therefrom. When the volume of the biogas formed under unit time is plotted against the time, the curve consists of three stages: a steep ascending stage, a horizontal stage (plateau) and a step descending stage. The total amount of the gas formed from the introduced methanol can be determined from the area under the curve by graphical integration (E. Siminovits, T. Szontagh: XI. Biochemical Conference (Sopron, 1970) lectures Nos. 59 and 60; T. Szontagh, E. Simonovits, I. Békés: XII. Biochemical Conference (Pécs, 1971), p. 219 to 225; T. Szontagh, E. Simonvits, I. Békés, E. Ezer, A. Laukó: XIII. Biochemical Conference (Szombathely, 1972), lecture No. 35).

The height of the plateau (expressed as produced gas, ml./5 l. of fermentation broth x hours) is a good measure of the actual biochemical activity of the given fermentation broth, therefore this figure was used to determine the amount of methanol which can be consumed by the population within 24 hours from a certain time. These values should always be taken into account in the control of the fermentation, because a higher increase in the amount of non-consumed methanol during the process exerts a toxic effect on the fermentation broth.

The amounts of methanol which may be supplied at or above the indicated minimum plateau heights are given in table 1.

Table 1

| Plateau height ml./5 l. of fermentation broth × hours | Supplied methanol v/v %/ fermentation broth |
|---|---|
| 560 | 0.5 |
| 700 | 0.6 |
| 820 | 0.7 |
| 930 | 0.8 |
| 1050 | 0.9 |
| 1160 | 1.0 |
| 1280 | 1.1 |
| 1400 | 1.2 |
| 1520 | 1.3 |
| 1630 | 1.4 |
| 1740 | 1.5 |

As is known, vitamin $B_{12}$ concentration can be determined according to the method described in the British patent specification No. 1,169,933. This method has given, however, varying for the fermentation broths prepared according to the invention, thus a new analytical method had to be developed for the determination of the vitamin $B_{12}$ content of the broth. According to this new method the analysis is carried out as follows:

125 ml. of distilled water, 23 ml. of a 10% aqueous ferric chloride solution and 1.5 ml. of a 10% aqueous sodium cyanide solution are added to 125 ml. of fermentation broth, and the pH of the mixture is adjusted to between 5.2 and 5.4 with a 40% aqueous sodium hydroxide solution. Thereafter the mixture is heated at 121°C for 20 minutes in an autoclave, and then the leached sample is sedimented in an angle-centrifuge. The supernatant liquid is decanted, the vitamin $B_{12}$ content of the aqueous solution is separated by solvent extraction and paper chromatography, thereafter the vitamin $B_{12}$ content is determined by extinction measurement at a wavelength of 580 nm. with a SPEKOL type spectrophotometer.

Since according to our examinations the centrifuged sediment still contains 10 to 20% of a liquid equivalent with the supernatant (and, consequently, a corresponding amount of the liberated vitamin $B_{12}$), the sediment is re-suspended in 125 ml. of water, centrifuged again, and the vitamin $B_{12}$ content of the resulting supernatant liquid, determined as described above, is added to the value obtained in the previous measurement. The amount of vitamin $B_{12}$ determined in this latter step may even be as high as 2000 to 5000 $\mu g./l.$ for fermentation broths with high (30,000 to 40,000 $\mu g./l.$) vitamin $B_{12}$ factors.

While the simple "hot digestion at 100°C" gives an adequate result for fermentation broths containing about 10,000 $\mu g./l.$ of vitamin $B_{12}$, in the fermentation broths with higher vitamin $B_{12}$ levels the vitamin $B_{12}$ (coenzyme) molecules can be separated from the presumed protein bond apparently only with a hydrolysis at higher temperatures. Since the efficiency of a processing method is determined by the proportion of separated vitamin $B_{12}$ and that present in the fermentation broth, it is essential to know as accurately as possible the value of vitamin $B_{12}$ present in the broth.

Accordingly, the invention relates to a process for the production of fermentation broth with increased vitamin $B_{12}$ content by a fermentation process carried out with a methane-producing mixed bacterium population under anaerobic septic conditions in the presence of known nutrient components and precursors, in which methanol, preferably in an amount of 0.5 v/v %, is added for some (2–4) days, preferably for 3 days to the fermentation broth containing vitamin $B_{12}$ used as starting substance; thereafter 10% of the fermentation broth is removed and an equal volume of a nutrient broth containing the usual components in tenfold concentrations is added periodically in every 5th –12th day, preferably in every 10th day, then the removal of fermentation broth is interrupted for 0 to 2 days, preferably for 1 day, and only 0.4 to 1.5 v/v% of methanol are added to the fermentation broth, and subsequently 10% of the fermentation broth is removed daily and an equal volume of a nutrient broth containing the usual components in the usual concentrations is added together with 0.4 to 1.5 v/v% of methanol, depending on the biogas production of the fermentation broth, and this series of operations is repeated periodically during the complete fermentation procedure taking into consideration the pH of the fermentation broth.

The invention thus comprises a process for the anaerobic septic fermentation of a broth to produce vitamin $B_{12}$ in the presence of bacterial nutrients, methanol and a methane-producing bacteria capable of fermenting methanol to produce vitamin $B_{12}$ wherein portions of the fermenting broth are periodically removed and replaced by a nutrient broth containing nutrient components in a normal concentration to sustain fermentation. The improvement of the invention comprises the combination of the following steps:

a. adding methanol in daily amounts of 0.4 to 0.7 volumes/volume % for two to four days to said fermenting broth;

b. thereafter monitoring the pH of said fermenting broth and upon the pH falling to 5.6 to 5.8 removing 5 to 15 volume % of the fermenting broth and replacing same with an equal volume of concentrated bacterial nutrient broth which contains the nutrient components in 5 to 12 times higher concentration than said normal concentrations, and repeating this step once during each interval of 5 to 12 days;

c. between repetitions of step (b) and each day for periods of five to ten days removing 5 to 15 volume % of the fermenting broth daily and replacing same with an equal volume of the bacterial nutrient broth with said nutrient compositions in said normal concentrations together with 0.4 1.5 volume % of methanol; and d. interrupting the removal of fermenting broth in step (c) for a period up to two days and adding only 0.4 to 1.5 volume % of methanol to the fermenting broth during the interruption.

Advantageously the methanol is added in step (a) for substantially three days, the fermenting broth is removed in step (b) and replaced with an equal volume of concentrated bacterial nutrient broth about every 10th day, the fermenting broth removal is interrupted in step (d) for a period of substantially 1 day, and the concentrated nutrient broth is added in step (b) only on the day that fermenting broth is removed while on all other days of the period of step (b) only methanol is added.

The main advantages of the process according to the invention can be summarized as follows:

1. The process provides, under certain conditions on a laboratory scale, high vitamin $B_{12}$ values that could not be attained so far with septic fermentation processes and can hardly be attained even with artificially activated monocultural fermentation processes. The high vitamin $B_{12}$ level, about 3.5 to 4 times higher than that of the average industrial scale processes (about 10,000 µg./l.) can be accomplished in laboratory scale with the synchronized periodical procedure of the invention with a 2 to 2.5-fold nutrient requirement and 3-fold methanol requirement compared to the average industrial values.

2. In the laboratory process, reproduced several times, vitamin $B_{12}$ levels of 30,000 to 35,000 µg./l. could be maintained for about a one-month semicontinuous fermentation process even in an iron fermenter of 50 m³. capacity (Example 4).

To the best of our knowledge, the synchronization technique has so far been used for scientific purposes only, such as for instance in the determination of the duplication times of bacteria. The process of the invention is the first one to utilize a synchronization technique in a fermentation procedure, and also the first to utilize this method for septic cultures consisting of several bacterium types. As known, all bacteria have different and more or less characteristic duplication periods; thus, in fact, a mixed population cannot be synchronized in a single process. In our process starvation is utilized for synchronization, thereby bringing the different bacteria into an approximately uniform repose (inactive) stage. The addition of the nutrient and energy sources to the thus-synchronized different bacteria in experimentally pre-determined intervals and amounts results in an optimum production of vitamin $B_{12}$, i.e. leads to the overproduction of the coccus-diplococcus bacteria with the best specific productivities as compared to the less productive rod bacteria.

The process of the invention is elucidated in detail by the following Examples.

EXAMPLE 1

5.1 each of an industrial fermentation broth produced by semicontinuous fermentation with methane producing bacteria vitamin $B_{12}$ content: 9,936 µg./l.) are introduced into two laboratory-scale fermenters with 5.1 working capacities, equipped with gas removal outlets. The fermenters are placed into a thermostat heated to 32°–34°C. On the first three days of the experiment no fermentation broth is removed, and only 25 ml. of methanol are added to each of the fermenters. On the fourth day 500 ml. of fermentation broth is removed, and 500 ml. of a concentrated broth with the following composition are supplied:

| | | |
|---|---|---|
| corn steep liquor | 24.0 | g. |
| hydrolyzed brewer's yeast (20%) | 5.0 | ml. |
| succinic anhydride | 0.03 | g. |
| cobalt chloride | 0.05 | g. |
| 5,6-dimethyl-benzimidazole | 0.015 | g. |
| magnesium chloride | 0.5 | g. |
| molasses | 10.0 | g. |
| sulfite waste liquor | 8.0 | g. |
| liver extract (10%) | 5.0 | ml. |
| glycine | 0.03 | g. |
| ammonium hydroxide (24%) | 5.5 | ml. |

-continued

| | | |
|---|---|---|
| diammonium hydrophosphate | 10.0 | g. |
| ammonium hydrocarbonate | 15.0 | g. |
| ammonium sulfate | 7.5 | g. |
| sodium bisulfate | 0.1 | g. |

In the following period of fermentation the above amount of the concentrated broth is fed into the fermenters on days 10, 17, 25, 33, 40, 46, 52, 60, 66 and 72 of the fermentation; prior to the administration of the broth 10% of the fermentation broth is removed. No fermentation broth is removed on days 5, 6, 7, 8, 9, 11, 12, 13, 14, 15, 16, 18, 19, 20, 21, 22, 23, 24, 26, 34, 41, 47, 53, 61, 67, 73 and 74 of the fermentation; on these days only methanol is introduced. On the remaining days of the fermentation 10% of fermentation broth is removed, and an equal volume of usual broth, containing the same components as listed above for the concentrated broth but in 10 times less concetrations, is introduced. The maximum amount of methanol is 75 ml. (1.5 v/v%); the actual amount is chosen according to Table 1.

The average vitamin $B_{12}$ level of the fermentation broths removed from the two parallel experiments during the semicontinuous process, i.e. from the 25th to the 75th day of fermentation, was as follows:

"A" fermenter: 43,268 μg. of vitamin $B_{12}$/l. of fermentation broth

"B" fermenter: 43,543 μg. of vitamin $B_{12}$/l. of fermentation broth

EXAMPLE 2

One proceeds as described in Example 1 with the difference that from the 4th day of fermentation 10% of the fermentation broth is removed daily, i.e. the semicontinuous fermentation is started on the 4th day instead of the 25th. The vitamin $B_{12}$ content of the fermentation broth used for induction was 10,600 μg./l.

The amount of methanol introduced daily is as follows:

| Day of fermentation | Amount of methanol |
|---|---|
| 3 to 9 | 40 ml. |
| 10 to 12 | 50 ml. |
| 13 to 14 | 60 ml. |
| 15 | 65 ml. |
| 16 | 70 ml. |
| 17 | 75 ml. |

In the further process the daily amount of methanol to be introduced depends on the plateau-height of the resulting biogas.

The amount of vitamin $B_{12}$ varies during the semicontinuous fermentation as follows:

| Day of fermentation | μg. of vitamin $B_{12}$/l. of fermentation broth |
|---|---|
| 2 | 12,400 |
| 4 | 11,700 |
| 8 | 16,800 |
| 10 | 14,900 |
| 11 | 16,200 |
| 14 | 14,900 |
| 15 | 16,200 |
| 16 | 19,872 |
| 17 | 23,124 |
| 18 | 25,400 |
| 21 | 23,124 |
| 22 | 23,200 |
| 28 | 21,432 |
| 31 | 26,400 |
| 32 | 27,700 |
| 35 | 25,944 |
| 36 | 26,600 |
| 37 | 32,800 |
| 38 | 32,200 |
| 39 | 33,270 |
| 43 | 28,152 |
| 44 | 30,400 |
| 45 | 32,200 |
| 46 | 27,200 |
| 49 | 30,500 |
| 50 | 31,600 |

EXAMPLE 3

4500 ml. of an industrial fermentation broth produced according to Hungarian patent specification No. 159,356 is filled into a laboratory-scale fermenter with a working capacity of 5 l., equipped with a gas-removing outlet. 500 ml. of a fermentation broth concentrate, obtained by the separation of an industrial fermentation broth, and containing 88,000 μg./l. of vitamin $B_{12}$, are added to the first broth. 75 ml. of methanol and an amount of concentrated broth as given in Example 1, are added to the obtained enriched fermentation broth with a calculated vitamin $B_{12}$ content of 18,500 μg./l., and the mixture is well stirred.

No fermentation broth is removed on the 2nd and 3rd days of operation; on these days only a daily amount of 75 ml. of methanol is added. Between days 4 and 10 of the operation a daily amount of 500 ml. of fermentation broth is removed, and 500 ml. of usual broth and 75 ml. of methanol are added to the remainder, i.e. the semicontinuous procedure is started. On the 11th day a concentrated broth is supplied again, and from this day on the procedure described in Example 2 is followed. Methanol is fed in daily amounts of 75 ml.

The amount of vitamin $B_{12}$ varies during the fermentation as follows:

| Day of fermentation | μg. of vitamin $B_{12}$/l. of fermentation broth |
|---|---|
| 5 | 22,632 |
| 6 | 19,320 |
| 7 | 20,424 |
| 10 | 21,016 |
| 11 | 21,200 |
| 12 | 27,000 |
| 13 | 33,400 |
| 14 | 32,000 |
| 17 | 36,310 |
| 20 | 36,690 |
| 21 | 35,548 |
| 22 | 35,880 |
| 23 | 30,968 |
| 26 | 39,800 |
| 27 | 33,450 |
| 28 | 34,166 |
| 29 | 36,250 |
| 30 | 36,200 |
| 33 | 28,900 |
| 34 | 35,780 |
| 35 | 30,360 |
| 36 | 30,800 |
| 37 | 33,000 |
| 43 | 30,500 |

-continued

| Day of fermentation | µg. of vitamin $B_{12}$/l. of fermentation broth |
|---|---|
| 44 | 33,000 |

The values completed with factor III, biologically equivalent with vitamin $B_{12}$, are as follows:

| | |
|---|---|
| 20 | 49,000 |
| 28 | 44,494 |
| 34 | 49,320 |

EXAMPLE 4

50 m³. of industrial fermentation broth produced according to Hungarian patent specification No. 159,356 (vitamin $B_{12}$ content: 9,936 µg./l.) are fed into a pilot-plant fermenter of 50 m³. working capacity. On the first 3 days of the operation 1 m³. of fermentation broth per day is removed, and 250 ml. of methanol and 750 ml. of water are introduced daily into the fermenter. On the fourth day 5 m³. of fermentation broth are removed, and 5 m³. of concentrated broth, with the same composition as described in Example 1, and 400 l. of methanol are introduced. Then, on days 5, 6, 7, 8, 9, 11, 12, 13, 15, 16, 17, 18, 19, 20, 21, 22, 24, 25, 26, 34, 43, 47, 51, 60, 66, 72, 74 and 75 of the fermentation 1 m³. of fermentation broth is removed, and only methanol is introduced.

On days 4, 10, 14, 23, 33, 42, 46, 50, 59, 65 and 71.5 m³. of fermentation broth are removed, and concentrated broth and methanol are added to the remainder. On the other days 5 m³. of fermentation broth are removed, and methanol and usual broth (with one-tenth of the concentration of the concentrated broth) are administered. The maximum daily amount of methanol is 750 l., the administration is carried out according to the data of Table 1.

The average concentration of vitamin $B_{12}$ in the fermentation broth between the 46th and 75th day of the procedure amounts to 32,748 µg./l. Although the semicontinuous operation started already at the 27th day, due to the difficulties arising from the increase in dimensions the average value is given from the 46th day only.

What we claim is:

1. In a process for the anaerobic septic fermentation of a broth to produce vitamin $B_{12}$ in the presence of bacterial nutrients, methanol, and a methane producing bacteria capable of fermenting methanol to produce vitamin $B_{12}$ and wherein portions of the fermenting broth are periodically removed and replaced by a nutrient broth containing nutrient components in a normal concentration to sustain fermentation, the improvement which comprises in combination the following steps:

a. adding methanol in daily amounts of 0.4 to 0.7 volumes/volume % for 2 to 4 days to said fermenting broth;
   b. thereafter monitoring the pH of said fermenting broth and upon the pH falling to 5.6 to 5.8 removing 5 to 15 volume percent of the fermenting broth and replacing same with an equal volume of a concentrated bacterial nutrient broth which contains the nutrient components in 5 to 12 times higher concentration than said normal concentrations, and repeating this step once during each interval of 5 to 12 days;
   c. between repetitions of step (b) and each day for periods of 5 to 10 days removing 5 to 15 volume percent of the fermenting broth daily and replacing same with an equal volume of the bacterial nutrient broth with said nutrient compositions in said normal concentrations together with 0.4 to 1.5 volume percent of methanol; and
   d. interrupting the removal of fermenting broth in step (c) for a period up to two days and adding only 0.4 to 1.5 volume percent of methanol to the ferming broth during the interruption.

2. The improvement defined in claim 1 wherein:
   the methanol is added in step (a) for substantially 3days;
   the fermenting broth is removed in step (b) and replaced with an equal volume of concentrated bacterial nutrient broth about every 10th day; and
   the concentrated nutrient broth is added in step (b) only on the day that fermenting broth is removed while on all other days of the period of step (b) only methanol is added.

* * * * *